(12) United States Patent
Nakamura et al.

US008030014B2

(10) Patent No.: US 8,030,014 B2
(45) Date of Patent: Oct. 4, 2011

(54) DETECTING AGENT AND THERAPEUTIC AGENT FOR HIGHLY MALIGNANT BREAST CANCER

(75) Inventors: Yasushi Nakamura, Wakayama (JP); Hironao Yasuoka, Wakayama (JP); Masahiko Tsujimoto, Osaka (JP); Rieko Goto, Kyoto (JP); Zenzaburo Tozuka, Osaka (JP); Kunio Momiyama, Osaka (JP); Kennichi Kakudo, Nara (JP); Tomonori Takami, Hyogo (JP)

(73) Assignee: JCL Bioassay Corporation (JP)

( * ) Notice: Subject to any disclaimer, the term of this patent is extended or adjusted under 35 U.S.C. 154(b) by 842 days.

(21) Appl. No.: 11/993,103

(22) PCT Filed: Dec. 8, 2006

(86) PCT No.: PCT/JP2006/325008
§ 371 (c)(1),
(2), (4) Date: Dec. 19, 2007

(87) PCT Pub. No.: WO2007/069709
PCT Pub. Date: Jun. 21, 2007

(65) Prior Publication Data
US 2010/0215648 A1    Aug. 26, 2010

(30) Foreign Application Priority Data
Dec. 14, 2005    (JP) .................................. 2005-361030

(51) Int. Cl.
*G01N 33/574*    (2006.01)
(52) U.S. Cl. ......... 435/7.23; 435/7.1; 436/501; 436/518
(58) Field of Classification Search ......................... None
See application file for complete search history.

(56) References Cited

U.S. PATENT DOCUMENTS
5,185,450 A    2/1993    Owen

FOREIGN PATENT DOCUMENTS
| JP | 63500245 | 1/1988 |
| JP | 2004151003 | 5/2004 |
| WO | 2004097030 | 11/2004 |

OTHER PUBLICATIONS

Klein et al Matrix Biol. 16:307-317, 1997.*
Berthod et al, J Invest Dermatol.108:737-742, 1997.*
Atherton et al, Cell Tissue Res 291: 507-511, 1998.*
Atherton, Amanda J. et al., "Differential expression of type XIV collagen/undulin by human mammary gland intralobular and interlobular fibroblasts", Cell and Tissue Research, vol. 291, No. 3, Mar. 1998, pp. 507-511.
Klein Gerd et al., "Cell Binding Properties of Collagen Type XIV for Human Hematopoietic Cells", Matrix Biology, vol. 16, No. 6, 1997/98, pp. 307-317.
Ehnis, Tobias et al., "Localization of a Binding Site for the Proteoglycan Decorin on Collagen XIV (Undulin)", The Journal of Biological Chemistry, vol. 272, No. 33, Aug. 15, 1997, pp. 20414-20419.
Tono-Oka, Shiro et al., "Transient Expression of Collagen Type XIV During Muscle Development and Its Reappearance After Denervation and Degeneration", The Journal of Histochemistry and Cytochemistry, vol. 44, No. 8, 1996, pp. 907-918.
Woelfle et al., "Molecular Signature Associated with Bone Marrow Micrometastasis in Human Breast Cancer", Cancer Res., vol. 63, pp. 5679-5684, Sep. 15, 2003.
Jacquemier et al., "Protein Expression Profiling Identifies Subclasses of Breast Cancer and Predicts Prognosis", Cancer Res., vol. 65, pp. 767-779, Feb. 1, 2005.
Lim et al., "Proteomics in Pathology Research", Lab Invest., vol. 84, pp. 1227-1244, Aug. 16, 2004.
Adam et al., "Comprehensive Proteomic Analysis of Breast Cancer Cell Membranes Reveals Unique Proteins with Potential Roles in Clinical Cancer", J. Biol. Chem., vol. 278, No. 8, pp. 6482-6489, Feb. 21, 2003.
Jessani et al., "Enzyme Activity Profiles of the Secreted and Membrane Proteome that Depict Cancer Cell Invasiveness", Proc. Natl. Acad. Sci. USA, vol. 99, No. 16, pp. 10335-10340, Aug. 6, 2002.
Schuppan et al., "Undulin, an Extracellular Matrix Glycoprotein Associated with Collagen Fibrils", J. Biol. Chem., vol. 265, No. 15, pp. 8823-8832, May 25, 1990.
Just et al., "Undulin is a Novel Member of the Fibronectin-Tenascin Family of Extracellular Matrix Glycoproteins", J. Biol. Chem., vol. 266, No. 26, pp. 17326-17332, Sep. 15, 1991.
Atherton et al., "Differential Expression of Type XIV Collagen/Undulin by Human Mammary Gland Intralobular and Intralobular Fibroblasts", Cell Tissue Res., vol. 291, pp. 507-511, 1998.
Ehnis et al., "A Chondroitin/Dermatan Sulfate Form of CD44 Is a Receptor for Collagen XIV (Undulin)", Exp. Cell Res., vol. 229, pp. 388-397, 1996.
Ennis et al., "Localization of a Binding Site for the Proteoglycan Decorin on Collagen XIV (Undulin)", J. Biol. Chem., vol. 272, No. 33, pp. 20414-20419, Aug. 15, 1997.
Paulus et al., "Characterization of Integrin Receptors in Normal and Neoplastic Human Brain", Am. J. Pathol., vol. 143, No. 1, pp. 154-163, Jul. 1993. Ruehl et al., "The Elongated First Fibronectin Type III Domain of Collagen XIV is an Inducer of Quiescence and Differentiation in Fibroblasts and Preadipocytes", J. Biol. Chem., vol. 280, No. 46, pp. 38537-38543, Nov. 18, 2005.
Gerecke et al., "Type XIV Collagen is Encoded by Alternative Transcripts with Distinct 5' Regions and is a Multidomain Protein with Homologies to von Willebrand's Factor, Fibronectin, and Other Matrix Proteins", J. Biol. Chem., vol. 268, No. 16, pp. 12177-12184, Jun. 5, 1993.
Pawitan et al., "Gene Expression Profiling Spares Early Breast Cancer Patients From Adjuvant Therapy: Derived and Validated in Two Population-Based Cohorts", Breast Cancer Research, vol. 7, No. 6, pp. 953-964, 2005, with Supplementary Report dated Aug. 18, 2005.
"New Drug Delivery System", First Edition, CMC Publishing Co., Ltd., Tokyo, pp. 165-167, Jan. 31, 2000.

* cited by examiner

*Primary Examiner* — Misook Yu
*Assistant Examiner* — Lei Yao
(74) *Attorney, Agent, or Firm* — The Webb Law Firm

(57) ABSTRACT

A detection agent for high malignancy breast cancer includes an antibody against collagen XIV, or a variant or derivative or fragment of the antibody. A therapeutic agent for high malignancy breast cancer includes a conjugate of an anticancer drug and an antibody against that protein, or a variant or derivative or fragment thereof. Accordingly, it is possible to easily and accurately detect and diagnose high malignancy breast cancer.

1 Claim, 5 Drawing Sheets

DETECTING AGENT AND THERAPEUTIC AGENT FOR HIGHLY MALIGNANT BREAST CANCER

TECHNICAL FIELD

The present invention relates to detection agents and therapeutic agents for high malignancy breast cancer. More specifically, it relates to reagents for detecting proteins specific to high malignancy breast cancer, and to therapeutic agents for high malignancy breast cancer by using antibodies against those proteins.

BACKGROUND ART

According to the report of 1998 on "Research on Increasing the Accuracy and the Utilization of the Population-Based Cancer Registry", supported by a Grant-in-Aid for Cancer Research from the Ministry of Health, Labour and Welfare, Japan, 33,676 cases of breast cancer are reported in one year, and the age-adjusted incidence rate was 52.2 cases per 100,000 persons, becoming the number one malignant neoplasm in women, and these figures have increased approximately three-fold since 1970. The number of breast cancer patients has been increasing year by year, and it is predicted to reach 48,000 cases, 56.9/10,000 persons by 2015. Because of breast cancer's relatively good prognosis, according to the 2001 report by Vital Statistics of Japan, Statistics and Information Department, Minister's Secretariat, Ministry of Health, Labour and Welfare, the mortality rate for breast cancer is fifth among cancer sites in female cancer patients, but from age 50 onward the mortality rate is high. The standardized death rate tends to be higher in urban areas, and a 1999 report by the Japan Cancer Society shows that the standardized death rate in the Tokyo Metropolis is 132.2%, compared to 73.5% in Kagoshima Prefecture. This increase in the number of breast cancer patients seems to be related to changes in our lifestyle in recent years, and example of the reasons include longer menstrual periods, postmenopausal hormone supplement therapy, and alcohol consumption.

Most breast cancer is invasive ductal carcinoma arising from duct epithelium. Appropriate surgical treatment and chemotherapy will bring the cancer into temporary remission, but metastasis often occurs from the earliest stages, and the cancer reappears after a number of years, then develops bone, liver, brain, and lung metastases (carcinomatous lymphangitis) and frequently leads to death. The 5-year survival rate is 90% in stage I cases in which the tumor is 2 cm or less and there is no lymph node metastasis. Whereas in stage III and IV cases with skin/chest wall infiltration and 10 or more of lymph node metastases or distant metastases, the 5-year survival rate is about 70%.

Lymph node metastasis is the most important prognosis factor that affects these survival rates. A systemic metastasis mechanism via lymph nodes is predicted in many types of breast cancer, and in recent years, breast cancer has been increasingly viewed as a systemic disease. There are few specific markers for diagnosing metastasis, and thus the diagnosis of metastasis is frequently made by diagnostic imaging using primarily ultrasound, or fine-needle aspiration cytology. Effective treatments include surgical excision as well as antihormonal therapy and preoperative chemotherapy, and at the current time, monoclonal antibody against HER2/neu (Herceptin) has been applied as a molecular target drug to cases having metastasis.

The average prognosis for breast cancer differs depending on the medical facility, and the 5-year survival rate is 80% or more. However, there is a very poor prognosis group with a 5-year survival rate of approximately 40%, and in particular, this group exhibits widespread (numerous) lymph node metastasis from earlier stages, regardless of the size of the tumor. This group is classified as invasive micropapillary carcinoma under the histological classifications of the World Health Organization, and inflammatory breast cancer is a representative example thereof. Some known factors for defining the degree of malignancy, the degree of local progress, and the metastasis of breast cancer include cell growth ability, estrogen receptor, progesterone receptor, and HER2 (Woelfe U. et al., Cancer Res., (2003) vol. 63, pp. 5679-5684; Jacquemier J. et al., Cancer Res., (2005) vol. 65, pp. 767-779; Lim S M. and Elenitoba-Johnson K S J., Lab Invest., (2004) vol. 84, pp. 1227-1244; Adam P J. et al., J. Biol. Chem., (2003) vol. 278, pp. 6482-6489; and Jessani N. et al., Proc. Natl. Acad. Sci. USA, (2002) vol. 99, pp. 10335-10340).

With regard to cancer metastasis, and particularly the metastasis of breast cancer, a method for comprehensively examining expression level of risk markers by using MUC1 and keratin19 in the bone marrow of breast cancer patients as risk markers and quantifying their level of mRNA expression has been developed (Japanese Laid-Open Patent Publication No. 2004-151003). However, at the current time, means or methods for easily detecting the malignancy of breast cancer is not yet sufficiently established.

SUMMARY OF THE INVENTION

It is an object of the present invention to provide a detection agent for easily detecting high malignancy breast cancer, and a therapeutic agent for high malignancy breast cancer.

The present invention provides a detection agent for high malignancy breast cancer, comprising:

an antibody against collagen XIV, or a variant or derivative or fragment thereof.

In one embodiment, the antibody or the variant or derivative or fragment thereof is labeled.

The present invention also provides a detection agent for high malignancy breast cancer, comprising:

a primer pair specific for a DNA encoding collagen XIV.

The present invention further provides a kit for detection and diagnosis of high malignancy breast cancer, comprising any of the detection agent described above.

The present invention provides a method for detecting high malignancy breast cancer in a cytological/histological specimen, comprising:

bringing a cytological/histological specimen into contact with an antibody against collagen XIV, or a variant or derivative, or fragment thereof; and detecting the antibody or the variant or derivative or fragment thereof bound to the cytological/histological specimen.

The present invention also provides a method for detecting high malignancy breast cancer in a cytological specimen, comprising:

preparing a cDNA from a cytological specimen;

performing PCR with the cDNA as a template and using a primer pair specific for a DNA encoding collagen XIV; and detecting a resultant PCR product.

The present invention further provides a therapeutic agent for high malignancy breast cancer, comprising:

a conjugate of an anticancer drug and an antibody against collagen XIV, or a variant or derivative or fragment thereof.

The present invention also provides a method of treating high malignancy breast cancer, comprising:

administering a conjugate of an anticancer drug and an antibody against collagen XIV, or a variant or derivative or fragment thereof in an effective amount to a high malignancy breast cancer patient.

In one embodiment, in the above-described therapeutic agent or method, the anticancer drug is selected from the group consisting of an anthracycline anticancer drug, a taxol anticancer drug, cyclophosphamide, and a fluorouracil derivative.

According to the present invention, it is possible to more precisely detect and diagnose high malignancy breast cancer. Thus, it is possible to judge the degree of malignancy of breast cancer, and it is possible to choose a preoperative and postoperative auxiliary chemotherapy regimen. By using the therapeutic agent for breast cancer of the present invention, it is possible to treat high malignancy breast cancer efficiently.

DETAILED DESCRIPTION OF THE INVENTION

Figure 1:
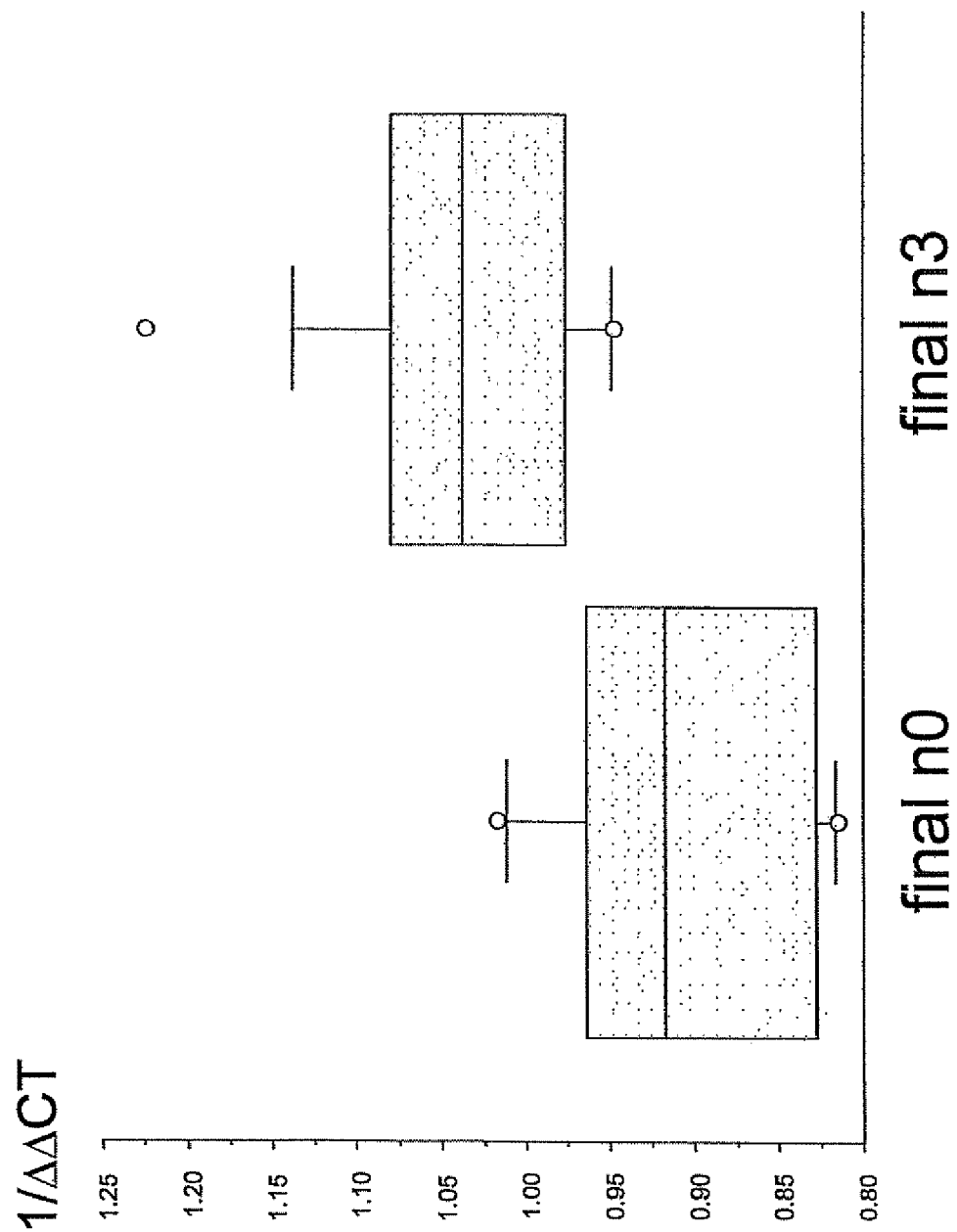
FIG. 1 is a graph that shows the amount of collagen XIVα1 gene expressed in the breast cancer tissue from the high malignancy breast cancer group (final n3) and the control group (final n0).

The present invention is based on the finding that collagen XIV is specifically expressed in high malignancy breast cancer. Hereinafter, the terms used in the present invention are defined and embodiments of the present invention are described.

Malignancy

The malignancy (or grade of malignancy) of cancer may be expressed in various ways, including biological, cytological, and histological malignancy. The malignancy is expressed vaguely rather than being strictly defined. Further, in general, the malignancy is graded as low, medium, and high malignancy. Pathologically, malignancy is determined by macroscopic findings such as the mode of growth and progress of cancer (invasive cancers are high malignancy) and the presence of formation of cancer metastasis (cancers with multiple metastases or metastases to a plurality of organs are high malignancy) and morphological findings such as atypism of cancer cells (morphological deviation from normal cells of the original site; recently, this has tended to be quantified by the degree of nuclear atypicality or the degree of histological atypicality) and the degree of differentiation (morphological deviation from the original site). In practice, cancer malignancy is often grouped by the degree of morphological differentiation and histological type.

In the present invention, the malignancy is defined by the grade of clinical malignancy, the tendency for local spread (cancer that form broad lesions in a short time are high malignancy), the tendency for metastasis (cancer that metastasize to multiple sites and organs in a short time are high malignancy), and the prognosis (cancer with a short survival time are high malignancy), for example. In the present invention, the prognosis serves as the largest factor for malignancy. Internationally, prognosis is most reflected by the staging (progress state; stage) defined by the TNM classification system (T: size and spread of tumor; N: presence and spread of lymph node metastasis, M: presence of metastasis). It should be noted that lower case letters or a p (pathological) added in front of the letter (such as pT, pN, or n) indicate determinations (final decisions) that have been made by examining an operation sample.

High malignancy refers to cancers with a poor prognosis. In the case of breast cancer, the factor influencing prognosis most is lymph node metastasis. In the present invention, a case where the tumor diameter is small and there is no distant metastasis (a candidate for surgical treatment) but in which there is a high degree of lymph node metastasis, that is, 10 or more of metastatic lymph nodes (n3), is defined as high malignancy (broad lymph node metastasis) breast cancer. For such cases, chemotherapy, including preoperative chemotherapy, with doxorubicin hydrochloride (adriamycin) or docetaxel hydrate (taxotere), and radiotherapy is ordinarily recommended. Postoperative auxiliary chemotherapy in which paclitaxel (taxol) is used in addition to adriamycin plus cyclophosphamide (AC), the current standard therapeutic regimen for breast cancer, lowers the annual mortality rate by 26% over AC therapy alone, however, the usage of the regimen is restricted because of increase in cardiotoxicity.

Collagen XIV

Collagen XIV (undulin; UND/UN) is an extracellular matrix present in interstitum, and is a large glycoprotein. It is loose and seen localized in dense collagen fiber, and has been related to mature collagen fiber (Schuppan D. et al., J. Biol. Chem., (1990) vol. 265, pp. 8823-8832). Collagen XIV is concsituted of 1780 amino acids, and in SDS polyacrylamide gel is a molecule having at least 1000 kDa (193,526 Da). Under reducing conditions, collagen XIV becomes polypeptides of 270 kDa, 190 kDa, and 180 kDa (Just M. et al., J. Biol. Chem., (1991) vol. 266, pp. 17326-17332). Collagen XIV has a triple helical structure in which three collagen XIV α1 chains (polypeptide chains, α chains) form a helical structure and which has S—S bonds in the homology region between collagen IX and collagen XII. Two isoforms resulting from differences in the carboxyl terminal part are known. They are UN1 from 8.5 kb, 6.5 kb, and 4.2 kb transcripts, and UN2 from a 5 kb transcript.

The protein has a structure of von Willebrand factor A homology region and a fibronectin or tenascin III-type homology region. UN1, has the short proline-rich segment of the carboxyl terminal followed by seven complete and one incomplete fibronectin III-type homology regions. UN2 has the unique acidic domain of the carboxyl terminal followed by two complete and one incomplete fibronectin III-type homology regions.

According to the Human Protein Reference Database (HPRD), tissue expressing collagen XIV includes skin, placenta, nervous system, muscle, liver, uterus, and blood vessel, and there are reports of expression in ligaments and synovial membranes as well. It has been reported that collagen XIV is expressed on the side of basement membrane of mesothelial cells in fetuses, although its role in development is not known. In mammary glands, collagen XIV is expressed in interlobular tissue, in contrast to collagen I. It is suggested that it may contribute to stabilizing collagens I and IV, which are ordinarily seen in stroma (Atherton A. et al., Cell Tissue Res., (1998) vol. 291, pp. 507-511). It has been reported that a chondroitin/dermatan sulfate form of CD44 (Ehnis T. et al., Exp. Cell Res., (1996) vol. 229, pp. 388-397), decorin (in vivo; proteoglycan (PG) II, PGII, PG40) (Ehnis T. et al, J. Biol. Chem., (1997) vol. 272, pp. 20414-20419), and integrin β1 (CD29) (Paulus W. et al., Am. J. Pathol., (1993) vol. 143, pp. 154-163) bind to collagen XIV. They are also reported as receptors for collagen XIV. It also has been reported that gelatinase (92 kDa) cleaves the collagen I domain. From these reports, it is predicted that collagen XIV plays a role in the control of functions important for development and differentiation, and of cell growth.

For the first time, the present invention demonstrates that collagen XIV is specifically expressed in high malignancy breast cancer. It should be noted that the expression of collagen XIV in cancers has been reported for odontogenic myxoma, ameloblastic fibroma (these are odontogenic tumors), brain tumors, and invasive pancreatic duct carcinoma. However, these reports have dealt only with the expression, and have not placed any meaning on that expression.

Detection and Diagnosis of Breast Cancer

By detecting a protein that is specifically expressed in high malignancy breast cancer, it is possible to judge the degree of malignancy of the breast cancer and to determine a preoperative and postoperative auxiliary chemotherapy regimen. Estimation of the prognosis and determination of the nature of the cancer based on the grade of malignancy is essential for the recent tailor-made medicine. High malignancy breast cancer requires the selection of systemic therapy that combines chemotherapy and radiotherapy. Thus, it is important for increasing survival time of patient and improving their QOL to diagnose malignancy based on prognosis factors and biomarkers, to select the preoperative and postoperative chemotherapy and to develop rapid treatment based on the diagnosis.

More specifically, the following three means for detecting and diagnosing high malignancy breast cancer are proposed:

(1) a minimally-invasive detection and diagnosis method using cytological material, in which PCR is used;

(2) a minimally-invasive detection and diagnosis method using cytological material, in which antibody is used; and (3) a detection and diagnosis method using tissue, in which antibody is used (including rapid diagnosis).

By illustrating a case where collagen XIVα1 serves as the target, the above-described (1) through (3) are described in more detail.

(1) Minimally-invasive detection and diagnosis method using cytological material, in which PCR is used At an initial consultation, for example, a sampling for cytological diagnosis is standardized. Thus, mRNA is extracted from a portion of the sampled cells and RT-PCR is performed to evaluate the collagen XIVα1 expression level and make a diagnosis of high malignancy breast cancer.

The following series of operations is performed using COL14A1 (gene encoding collagen XIVα1) specific primer.

(1-a) Cells are obtained by ultrasound guided fine-needle aspiration biopsy from a mammary gland tumor mass using a 21-23 gauge needle, for instance;

(1-b) The obtained cells are washed with an isotonic solution such as saline and centrifuged at 1200 rpm for five minutes to prepare cell sediment. Alternatively, cancer cells are isolated from a cytological specimen that has been prepared normally by quick mount or dissection. Using these cells, mRNA is extracted directly or all RNA is extracted with a kit employing an oligo-dT method or a guanine method, which are ordinarily used by those skilled in the art;

(1-c) Using the mRNA or total RNA as a template, reverse transcription with reverse transcriptase is performed as is ordinarily performed by those skilled in the art to prepare ssDNA (cDNA);

(1-d) Quantitative or semi-quantitative PCR is performed from the cDNA using COL14A1 specific primer to detect and quantify the COL14A1 expression product (collagen XIVα1); and (1-e) A diagnosis whether or not the cancer is high malignancy breast cancer is made by comparing the amount of collagen XIVα1 expression against a cutoff value.

(2) Minimally-invasive detection and diagnosis method using cytological material, in which antibody is used An immunocytochemical method is performed, using a cytological specimen prepared for diagnosis and using an antibody against collagen XIVα1, to detect and score collagen XIVα1 expression and thereby make a diagnosis of high malignancy breast cancer.

The following series of operations is performed using an anti-collagen XIVα1 antibody, for example.

(2-a) Cells are obtained by ultrasound guided fine-needle aspiration biopsy from a mammary gland tumor mass using a 21-23 gauge needle, for instance;

(2-b) The obtained cells are smeared directly onto the slide glass or washed with an isotonic solution such as saline and centrifuged at 1200 rpm for five minutes to prepare cell sediment. Then the sediment is smeared onto the slide glass. After smearing, the cells are wet fixed with 95% ethanol or a fixing agent that contains ethanol to prepare a cytological specimen;

(2-c) Using the cytological specimen prepared, immunocytochemistry is performed as illustrated below in (2-c-1) through (2-c-5), for example:

(2-c-1) The cells are made hydrophilic using phosphate buffered saline (PBS), for example;

(2-c-2) Non-specific adsorption reactions due to albumin, etc., are inhibited;

(2-c-3) Anti-collagen XIVα1 antibody is dropped on the specimen, to perform the primary reaction;

(2-c-4) The unreacted antibody is washed with a washing agent, and a secondary antibody is added to perform a secondary reaction;

(2-c-5) The unreacted antibody is washed and then an appropriate substrate is used to develop a color in the specimen, and the positive images are examined under a microscope; and (2-d) The positive image of the cytoplasm is scored in four grades, from negative 0 to strong positive 3+, and the strong positives are judged to be high malignancy breast cancer.

The anti-collagen XIVα1 antibody used here may be a directly-labeled anti-collagen XIVα1 antibody. This case may be a rapid diagnosis method, and the operations of (2-c-3) through (2-c-5) may be performed as shown below in (2-c-3').

(2-c-3') The prepared cytological specimen is reacted with anti-collagen XIVα1 antibody labeled with peroxidase, for instance.

(3) Detection and diagnosis method using tissue, in which antibody is used

An immunocytochemical method is performed using a tissue specimen for cytological/histological diagnosis that has been prepared for diagnosis and using an antibody against collagen XIVα1, to detect and score collagen XIVaI expression and thereby make the diagnosis of high malignancy breast cancer.

The following series of operations is performed using anti-collagen XIVα1, for example.

(3-a) A specimen is obtained from a mammary gland tumor mass through any of the following operations. A stamped cytological specimen or a frozen resected tissue is fixed with ethanol or a formalin solution, for example. Needle biopsy and resected specimens are fixed with formalin, and a tissue specimen for cytological/histological diagnosis is prepared by a method ordinarily performed by those skilled in the art;

(3-b) Using the prepared tissue specimen for cytological/histological diagnosis, immunocytochemistry is performed as illustrated below in (3-b-1) through (3-b-5), for example:

(3-b-1) Cells are made hydrophilic using phosphate buffered saline (PBS), for example;

(3-b-2) Using methanol containing 3% (v/v) peroxide, for example, endogenous peroxidase activity and non-specific adsorption reactions due to albumin, etc., are inhibited;

(3-b-3) Anti-collagen XIVα1 antibody is dropped on the specimen to perform the primary reaction;

(3-b-4) The unreacted antibody is washed with a washing agent, and then a secondary antibody is added to perform a secondary reaction;

(3-b-5) The unreacted antibody is washed and then an appropriate substrate is used to develop a color in the specimen, and the positive images are examined under a microscope; and (3-c) The positive images of the cytoplasm are scored in four grades, from negative 0 to strong positive 3+, and the strong positives are judged to be high malignancy breast cancer.

More specifically, a directly-labeled anti-collagen XIVα1 antibody may be used as the anti-collagen XIVα1 antibody. This case may be a rapid diagnosis method, and the operations of (3-b-3) through (3-b-5) may be performed as shown below in (3-b-3').

(3-b-3') The prepared tissue specimen for cytological/histological diagnosis is reacted with anti-collagen XIVα1 antibody labeled with peroxidase, for instance.

With a method from (1) through (3), protein that is specifically expressed in high malignancy breast cancer is detected, and when a diagnosis of high malignancy breast cancer is made, it is possible to choose a preoperative/postoperative auxiliary chemotherapy regimen as discussed above.

Since the DNA sequence encoding a protein that is specifically expressed in high malignancy breast cancer (for example, NCBI genbank accession No. NM 21110) is known, the specific primer used in means (1) can be suitably chosen by a person skilled in the art based on that DNA sequence.

The antibody used in means (2) and (3) can be an antibody against a protein that is specifically expressed in high malignancy breast cancer, or a variant or derivative or fragment of the antibody. Preferably, it is a specific antibody against a functional site of a protein that is specifically expressed in high malignancy breast cancer. The antibody can be a polyclonal antibody or a monoclonal antibody, and preferably is a monoclonal antibody. The antibody can be produced by a method ordinarily used by persons skilled in the art. It is also possible to use a commercially-available antibody. The antibody may also be suitably labeled with a marker that is ordinarily used by persons skilled in the art (enzyme, radio-isotope, fluorescent molecule, etc.).

The diagnostic means (1) through (3) preferably may be carried out using a diagnostic kit that includes the above specific primer or specific antibody. Such a diagnostic kit includes at least the specific primer or the specific antibody, and may also suitably include other reagents necessary for the diagnostic means.

The diagnosis of the grade of breast cancer malignancy may also be performed by combining a means for detecting a protein that is specifically expressed in high malignancy breast cancer and another conventional means for detecting cancer markers (for example, the breast cancer metastasis rapid diagnostic technique CK19-OSNA: see Japanese Laid-Open Patent Publication No. 2004-151003).

Treatment of Breast Cancer

To treat breast cancer, it is possible to use molecular target therapy in which a protein that is specifically expressed in high malignancy breast cancer is targeted. Specifically, it is possible to use a conjugate which is obtained by chemically modifying the antibody against a protein specifically expressed in high malignancy breast cancer or variant or derivative or fragment thereof with an anticancer drug. The antibody can be a polyclonal antibody or a monoclonal antibody, and preferably is a monoclonal antibody. Preferably, the antibody is a specific antibody for a functional site of a protein that is specifically expressed in high malignancy breast cancer. Such an antibody can be produced by a method ordinarily used by persons skilled in the art, or it is possible to use a commercially-available antibody.

When collagen XIVα1 is targeted, for example, such conjugates include (i) anti-collagen XIVα1 antibody-anticancer drug conjugates obtained by crosslinking the anti-collagen XIVα1 antibody with an anthracycline anticancer drug such as adriamycin via an amide group; (ii) anti-collagen XIVα1 antibody-anticancer drug conjugates of anti-collagen XIVα1 antibody and a Taxol anticancer drug such as paclitaxel (taxon or docetaxel hydrate (taxotere); (iii) anti-collagen XIVα1 antibody-anticancer drug conjugates of anti-collagen XIVα1 antibody and cyclophosphamide; and (iv) anti-collagen XIVα1 antibody-anticancer drug conjugates of anti-collagen XIVα1 antibody and a fluorouracil derivative.

The therapeutic agent for breast cancer of the present invention includes a conjugate of an anticancer drug with an antibody against a protein that is specifically expressed in high malignancy breast cancer or a variant or derivative or fragment thereof. Such conjugates can be suitably produced by a method ordinarily used by persons skilled in the art. Examples of conjugates include a disulfide hinge produced by a maleimide method or a pyridyl disulfide method; a conjugate of an antibody and an anticancer drug with thiol group-amino group bonding that is achieved using a hetero-bifunctional crosslinker such as sulfo-SMCC (sulfosuccin-imidyl-4-(N-maleimidometyl)cyclohexane-1-carboxylate); a conjugate of an antibody and an anticancer drug with carboxyl group-amino group bonding; and a conjugate of an antibody and a drug that is a target directed drug.

The therapeutic agent for breast cancer of the present invention can contain a pharmaceutically acceptable carrier ordinarily used in drug manufacture. There are no particular limitations regarding the form of the therapeutic agent for breast cancer. Depending on the form to be administered, it can be prepared as tablets, capsules, granules, injections, or implants, for example. For parenteral administration, it can be in the form of a sterilized aqueous or nonaqueous solutions, suspensions, or emulsions.

Examples of pharmaceutically acceptable carriers that can be used in injections or the like include various aqueous carriers, such as water, buffered water, and saline solution. Other appropriate vehicles include polypropylene glycol, polyethylene glycol, vegetable oil, gelatin, hydrogenated naphalene, and organic esters for injection such as ethyl oleate. The therapeutic agent of the present invention may also include auxiliary substances such as preservatives, moistening agents, buffering agents, emulsifiers, and/or dispersing agents. In implants, a biocompatible or biodegradable lactide polymer, lactide/glycoside copolymer, or a polyoxyethylene-polyoxypropylene copolymer may be contained in order to control the release of the active ingredient. Examples of pharmaceutically acceptable carriers for oral administration include excipients such as lactose, dextrin, sucrose, mannitol, corn starch, sorbitol, and crystalline cellulose, and adjuvants such as polyvinylpyrrolidone. These may be used alone or suitably combined with one another. Further, additives such as flavorings, coloring agents, and sweetening agents may be used suitably. These therapeutic agents for breast cancer can be produced by a method appropriate for each form. The amount of additive can be appropriately determined by persons skilled in the art.

The therapeutic agent for breast cancer of the present invention may be administered orally or parenterally. Preferably, it can be parenterally administered locally or systemically.

The amount of active ingredient to be combined with the carrier material for production of a single-dosage form varies depending on the individual to be treated and the mode of administration. In general, the therapeutic agent for breast cancer should be administered in an amount sufficient to reduce or eliminate breast cancer in a breast cancer patient (that is, an effective amount).

The therapeutic agent for breast cancer can be administered in a single dose or in several divided doses. In general, multiple anticancer drugs are combined together and thus single doses must be administered multiple times in four to six cycles every three or four weeks, for a total administration period of about 12 to 24 weeks. When Herceptin (general name: trastuzumab) is used, even though it must be continuously administered weekly by intravenous injection for 90 minutes, the desired amount of administration normally should be administered with a small number of intervals of at least several days each. The dose can be adjusted depending on various factors, such as the administration time; the administration route; the nature of the therapeutic agent; the rate of excretion; the severity of cancer; and the patient's age, body weight, and health condition. For example, FEC therapy (combination of fluorouracil, epirubicin, and cyclophosphamide) involves the administration of fluorouracil at 500 mg/m$^2$ and cyclophosphamide at 500 mg/m$^2$ per patient body surface area, in addition to the administration of epirubicin at a range from 50 to 100 mg/m$^2$ once every three weeks, and is commonly repeated for six cycles taking into consideration the patient's age and overall condition. In the case of paclitaxel, 80 to 100 mg/m$^2$ is administered weekly, and 175 to 210 mg/m$^2$ is administered every three weeks, and this cycle is repeated four times.

EXAMPLES

Example 1

Comprehensive Protein Analysis for a Target Molecule Relating to High Malignancy Breast Cancer (Breast Cancer with Widespread Lymph Node Metastasis)

(Subject)

Cases in which 10 or more lymph node metastases on the same side (pN3) were histologically confirmed upon initial consultation or initial surgery were defined as high malignancy breast cancer, according to the UICC (union internationale contrele cancer) sixth edition (2002) (breast cancer with widespread lymph node metastasis). Invasive micropapillary carcinoma (IMPC) as defined in WHO Classification of Tumours, Pathology and Genetics of Tumours of the Breast and Female Genital Organs (2003), edited by the World Health Organization/International Agency for Research on Cancer, also was included in the above. Thirteen cases of high malignancy breast cancer and 6 cases as controls which were negative for lymph node metastasis as confirmed molecular-biologically by RT-PCR (breast cancer metastasis rapid diagnostic technique CK19-OSNA: see Japanese Laid-Open Patent Publication No. 2004-151003) using cytokeratin 19 as a marker, were used as subjects (Table 1).

TABLE 1

| Sample number | Final n | Lymph node metastases/Lymph node |
|---|---|---|
| No lymph node metastases (n0; RT-PCR confirmed) | | |
| 1 | 0 | 0/23 |
| 2 | 0 | 0/15 |
| 3 | 0 | 0/3 |
| 4 | 0 | 0/21 |
| 5 | 0 | 0/3 |
| 6 | 0 | 0/29 |
| High malignancy group (n10/n-massive) | | |
| 7 | 3 | 13/18 |
| 8 | 3 | 14/20 |
| 9 | 3 | 14/24 |
| 10 | 3 | 21/30 |
| 11 | 3 | 32/33 |
| 12 | 3 | 11/14 |
| 13 | 3 | 42/42 |
| 14 | 3 | 12/23 |
| 15 | 3 | 19/31 |
| 16 | 3 | 42/42 |
| 17 | 3 | 48/48 |
| 18 | 3 | 16/19 |
| 19 | 3 | 18/48 |

Here, invasive micropapillary carcinoma (IMPC) is a type of invasive ductal carcinoma that has been classified relatively recently, and constitutes approximately 2% of all breast cancers. The average age is 59 years, which is the same as for general invasive ductal carcinomas. Invasive micropapillary carcinoma resembles primary micropapillary carcinomas of the bladder, which also have a poor prognosis. These are extremely malignant, and approximately 95% of cases exhibit lymph node metastasis as judged from the diagnosis. There have also been reported that the prognosis is similar to other tissue types, taking into account lymph node metastasis, tumor diameter, and prognostic factors. Lymph node metastasis is the greatest prognostic factor for breast cancer, and this tissue type can be considered to fall into the poor prognosis group due to the fact that a high degree of lymph node metastasis is involved. Histologically, a micropapillary component is seen in up to approximately 5% of all cases of breast cancer, regardless of whether or not the breast cancer is IMPC, but the amount of micropapillary component does not affect the prognosis. In the resected specimen, the average tumor diameter is approximately 2 cm (0.1 to 10 cm), and histologically a papillary mass or morula-like epithelial mass lacking triangular vasculature is formed. Further, the formation of interstitial fissures is present, and the tumor is accompanied by fibrous and sclerotic interstitium. Ordinarily, the histological grade is high, and a high degree of vasculature and lymph node invasion is observed (shows an image of tumor cells swimming within a lymphatic vessel-like lumen filled with a watery or mucoid substance). This is believed to be caused by an inversion of polarity, which can be confirmed by epithelial membrane antigen (EMA), for example. Both lymph node metastatic lesions and pleural effusion infiltrating cancer cells have the same histology as the primary lesion. The classical prognosis factors are bcl-2+: 70%, ER+: 70%, PgR+: 45%, HER2+: 36%, p53+: 12%. In terms of the molecular biology, the loss of the long arm of chromosome S has been reported.

(Procedure)

In addition to the 13 cases of high malignancy breast cancer, cryopreserved resected tissue from 6 cases in which lymph node metastasis is not observed histologically also were used. Each tissue was treated with collagenase to separate into cells. The separated cells were disrupted in a suitable buffer using a homogenizer, then centrifuged at an appropriate rotating speed (rpm). The cytoplasm, nucleus, and membrane were fractioned by the differences in the buffer composition and the rpm of the centrifuge. The cytoplasmic fraction was reduced with DTT/ammonium bicarbonate, then S-carboxamide-methylated with iodoacetamide followed by digestion with trypsin for 12 to 16 hours at 37° C. The enzyme reaction was stopped by adjusting pH to 2 through 3 with trifluoroacetic acid (TFA). After digestion, a sample which was obtained by tryptic digestion to degrade the proteins into peptides was injected into a two-dimensional liquid chromatograph (2DLC; made by Michrom BioResources, Inc.). The injected sample was loaded onto an ion-exchange column SCX Microtrap (made by Michrom BioResources, Inc.), and then eluted with 25 mM, 50 mM, 100 mM, 150 mM, 200 mM, and 500 mM ammonium formate. Then, the eluted fractions were loaded onto a reverse phase column Magic C18 (made by Michrom BioResources, Inc.), and eluted by applying a concentration gradient from 10 to 98% (v/v) acetonitrile/0.1% (v/v) formic acid. The eluted peptides were then introduced into an ion trap type mass spectrometer (LTQ/MS/MS; made by Thermo Electron) and subjected to a full MS scan ranging from m/z 150 to 2000. Then, the peptide fragments were detected by MS/MS measurement. Using the search software SEQUEST, the measured MS/MS spectra were matched with a database and a list of protein candidates that include peptide fragments with matching molecular weights was created.

Next, the screening method described below was used to screen proteins expressed specifically in the high malignancy breast cancer cases from the list of proteins in the cytoplasmic fraction of these cases.

(1) For each sample of the high malignancy breast cancer cases (13 cases), the average value of the indexes for identifying a protein (score) was calculated for each item for specifying a protein (accession number). This was taken as the index (score) for each protein in model of high malignancy breast cancer cases.

(2) Like in (1), for each sample of the cases in which lymph node metastasis is not observed histologically (6 cases), the average value of the indexes for identifying a protein (scores) was calculated for each item for specifying a protein (accession number). This served as the index (score) of protein in model of the control group.

(3) The differences between the indexes (scores) of the proteins in the model groups obtained in (1) and (2) were calculated. The data were rearranged so as to order the data based on their usefulness as information on the specific proteins. The scores in these of the proteins rearranged at the top were compared and evaluated for the various cases to identify specific protein candidates.

(Results)

<I-a> Specification of Target Molecules of High Malignancy Breast Cancer (Breast Cancer with Widespread Lymph Node Metastasis) by 2DLSC-LTQ/MS/MS Histopathological analysis shows that high malignancy breast cancer often exhibits a drop in adhesion with the interstitia and an inversion of polarity in cancer cells. In view of this, we focused our attention on collagen XIV, which is believed to have an anti-adhesive action.

TABLE 2

| Sample number | Final n | score |
|---|---|---|
| 1 | 0 | 12.17 |
| 2 | 0 | 22.12 |
| 3 | 0 | 0 |
| 4 | 0 | 22.11 |
| 5 | 0 | 36.13 |
| 6 | 0 | 24.14 |
| 7 | 3 | 38.14 |
| 8 | 3 | 48.13 |
| 9 | 3 | 74.51 |
| 10 | 3 | 132.32 |
| 11 | 3 | 140.25 |
| 12 | 3 | 82.16 |
| 13 | 3 | 44.13 |
| 14 | 3 | 88.22 |
| 15 | 3 | 70.34 |
| 16 | 3 | 112.28 |
| 17 | 3 | 110.24 |
| 18 | 3 | 62.23 |
| 19 | 3 | 96.26 |

The result of proteome analysis showed that collagen XIV has a difference value of 78.774, and when compared to the N-average score of 19.444, it was clear that collagen XIV was significantly expressed in high malignancy breast cancer.

<I-b> Confirmation of COL14A1 Expression in High Malignancy Breast Cancer (Breast Cancer with Widespread Lymph Node Metastasis) by Quantitative RT-PCR From frozen tissue of the breast cancer cases of interest, mRNA was extracted to prepare cDNA, and then quantitative (RT-) PCR was performed using a TaqMan probe method to evaluate the amount of gene expression.

Specifically, first, the frozen tissue was sliced to 100 µm tissue specimens with a Leica cryostat (frozen section microtome). Using a Microprep mRNA extraction kit (Amersham), mRNA was directly extracted and treated with DNase I (Ambion), and then using the mRNA as a template, reverse transcription (ThermoScript, Invitrogen) was performed with oligo (dT) 20 primer at 55° C. for 60 minutes to obtain cDNA. Quantitative PCR was performed with a TaqMan probe method using the cDNA prepared as above, and the amount of gene expression was measured. Assay-on-Demand inventoried Hs000385388 ml (NM 021110) by Applied biosystem (ABI) was used as the primer/probe mixture, TaqMan 2× mastermix (ABI), and GAPDH intrinsic expression control Primer/probe mix by ABI (4326317E, NM 002046) as the intrinsic control were used. The reaction and the measurement were performed by ABI prism 7100 sequence detector (ABI), and intrinsic control correction was performed with $\Delta\Delta$ CT method and the result was taken as the amount of gene expression. The result is shown in FIG. 1.

As seen from FIG. 1, the mRNA expression of COL14A1 was significantly higher in the high malignancy breast cancer case (final n3) group. The Wilcoxon/Kruskal-Wallis rank sum test one-way test showed a p value of 0.0353, which indicates that the mRNA is significantly expressed in high malignancy breast cancer.

In this way, the collagen XIVα1 molecule was identified by mass spectrometry as a target involved in high malignancy (widespread lymph node metastasis) breast cancer, which among general breast cancer has lymph node metastasis at an early stage and has a poor prognosis for life. The collagen XIVα1 was also evaluated in terms of mRNA and protein expression. It was found that collagen XIV is specifically expressed in high malignancy breast cancer and has the potential for clinical application as a biomarker, including as a prognosis factor, and also that collagen XIV can become a target of treatment.

Example 2

Figure 2:
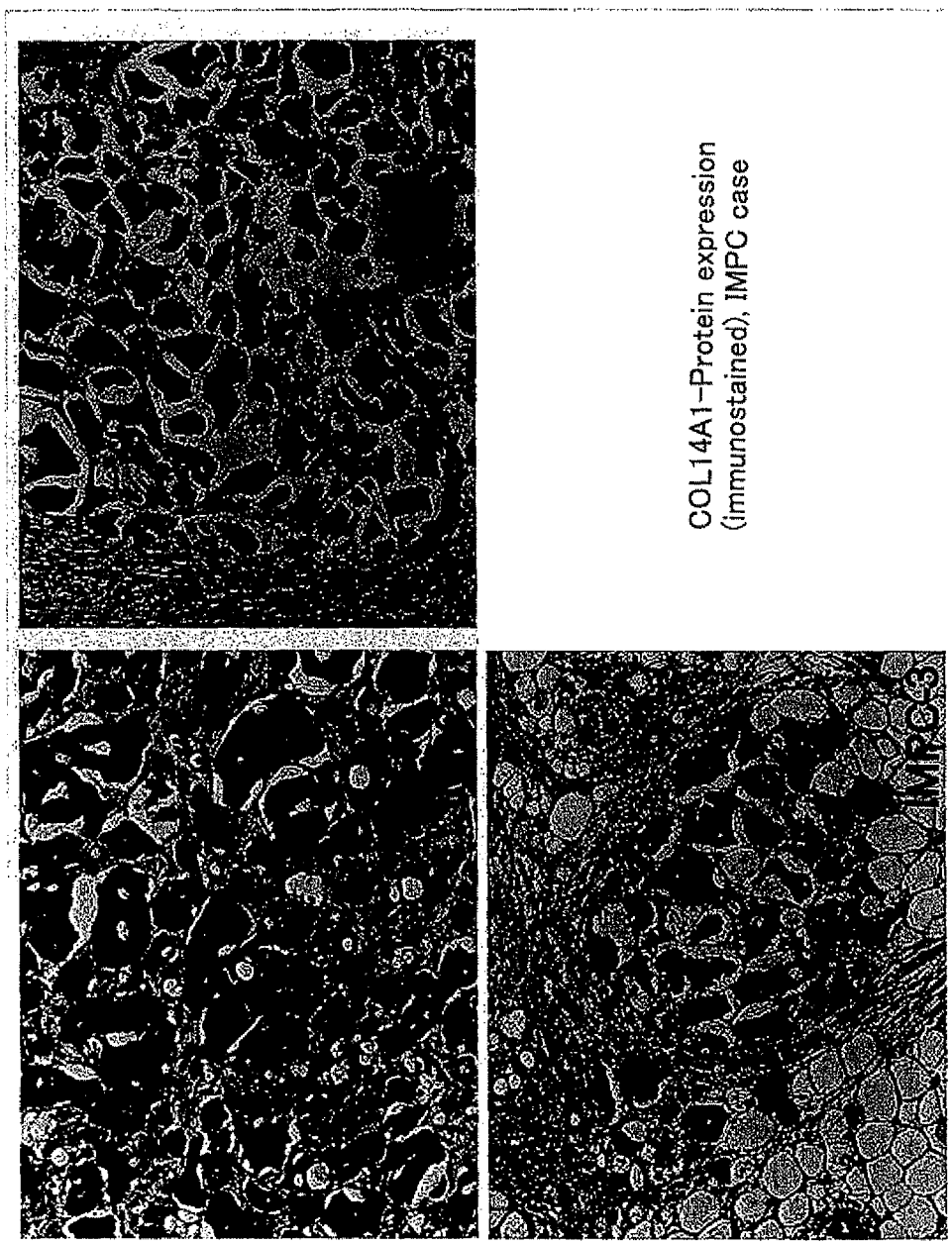
FIG. 2 shows micrographs of immunostained specimens of the breast cancer tissues from IMPC cases.

Analysis of Collagen XIVα1 Expression in High Malignancy Breast Cancer (Breast Cancer with Widespread Lymph Node Metastasis) Tissue Using a formalin fixed paraffin embedded specimen, immunohistochemistry was performed using an antibody against collagen XIVα1 to examine the protein expression.
(Subject)
Four cases of IMPC (invasive micropapillary carcinoma) and four cases of the high malignancy breast cancer (breast cancer with widespread lymph node metastasis) (final n3) of Example 1 that contained an IMPC component, for a total of eight cases, were tested.
(Procedure)
Specimens for immunostaining were prepared by slicing to 4 μm specimens with a microtome from a block of formalin fixed paraffin embedded specimen. The deparaffinization of the specimen was performed with a series of xylol and ethanol, and the specimen was subjected to hydrophilic treatment with phosphate buffered saline (PBS). Then, methanol containing 3% (v/v) hydrogen peroxide was added thereto to inhibit intrinsic peroxidase activity. After washing with PBS, a protein block serum-free (Dako) was added thereto to inhibit non-specific adsorption. Anti-collagen XIVα1 (LSL, LB-1400, MAP antibody) was diluted by a dilution factor of 100 with PBS-bovine serum albumin and this was added dropwise onto the specimen and allowed to react at 4° C. overnight. Excess antibody was washed with 0.1% Tween 20-supplemented Tris buffered saline (T-TBS, pH 7.4), then peroxidase polymer-labeled anti-mouse F(ab)' antibody (Nichirei Corporation: Histofine simple stain MAX-PO multi) was added thereto. The mixture was allowed to react at room temperature for 60 minutes. After washing with T-TBS, the specimen was color-developed by 0.02% (w/v) diaminobenzidine and PBS containing 0.01% (v/v) hydrogen peroxide, and the reaction was stopped by addition of tap water. The nucleus in the specimen was stained with Meyer's hematoxylin and made transparent by a series of ethanol and xylol. The specimen was then mounted by malinol, and examined under a microscope and evaluated for cytoplasm positive images.
(Results)
The results are shown in Table 3. A representative micrograph of a stained specimen (objective magnification ×10) is shown in FIG. 2. The expression of collagen XIVα1 protein was observed in the high malignancy breast cancer cases, and in particularly in the IMPC cases, as strong positive images (darkly stained portions). Immunohistochemistry using tissue sections was employed, and clear expression at the protein level was observed in some of the invasive ductal carcinoma having an IMPC component.

TABLE 3

| Sample number | Type | Final n | Expresion of collagen XIVα1 protein |
|---|---|---|---|
| 9 | IMPC+ | 3 | + |
| 16 | IMPC+ | 3 | + |
| 17 | IMPC+ | 3 | + |
| 18 | IMPC+ | 3 | + |
| IMPC-1 | IMPC | 3 | + |
| IMPC-2 | IMPC | 3 | + |
| IMPC-3 | IMPC | 3 | + |
| IMPC-4 | IMPC | 3 | + |

Example 3

Synthesis of Doxorubicin-Bound Anti-Collagen XIV Antibody

According to the procedure described below, the anticancer drug doxorubicin was bound to a spacer (first reaction and second reaction) and then conjugated with anti-collagen XIV antibody (final reaction).
<Detection Method>
In this example, the reaction product was confirmed by thin layer chromatography (TLC) and LC/MS. Both of these detection methods are described below.
(1) TLC
TLC was performed using water-saturated n-butanol/acetic acid (8:1, v/v) as the developing solvent, and the reaction product was detected with 365-nm UV light.
(2) LC/MS
HPLC was performed using the Alliance 2690 Separation Module (made by Waters), and the HPLC conditions were as follows:
(a) For confirming the first reaction
Column: Mightysil RP-18 (L) GP, 5 μm, 4.6×250 mm
Column temperature: 30° C.
Flow rate: 0.7 mL/min
Mobile phase: A solvent: water/methanol/acetic acid (90:10:0.1, v/v/v)
B solvent: methanol/acetic acid (100:0.1, v/v)
Gradient: A:B (30:70) 0 to 20 min→A:B (0:100) 20 to 35 min→A:B (30:70) 35 min onward
(b) For confirming the second reaction
Column: Mightysil RP-18 (L) GP, 5 μm, 4.6×250 mm.
Column temperature: 30° C.
Flow rate: 0.7 mL/min
Mobile phase: A solvent: water/methanol/acetic acid (90:10:0.1, v/v/v)
B solvent: methanol/acetic acid (100:0.1, v/v)
Gradient: A:B (40:60) 0 to 20 min→A:B (30:70) 20 to 30 min→A:B (0:100) 30 to 50 min→A:B (40:60) 50 min onward
For the MS, a linear ion trap LTQ MS (made by Thermo Electron) was used, and the conditions were as follows:
Ionization mode: ESI
Polarity: negative
Sheath gas: nitrogen, flow rate 45 arb
Spray voltage: 4 kV
Capillary temperature: 300° C.

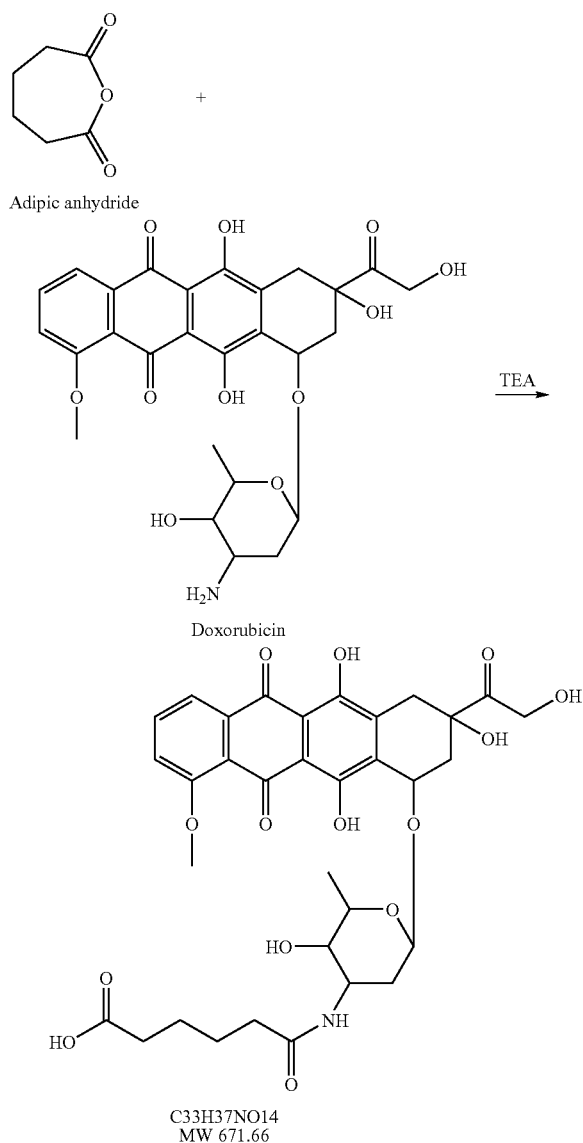

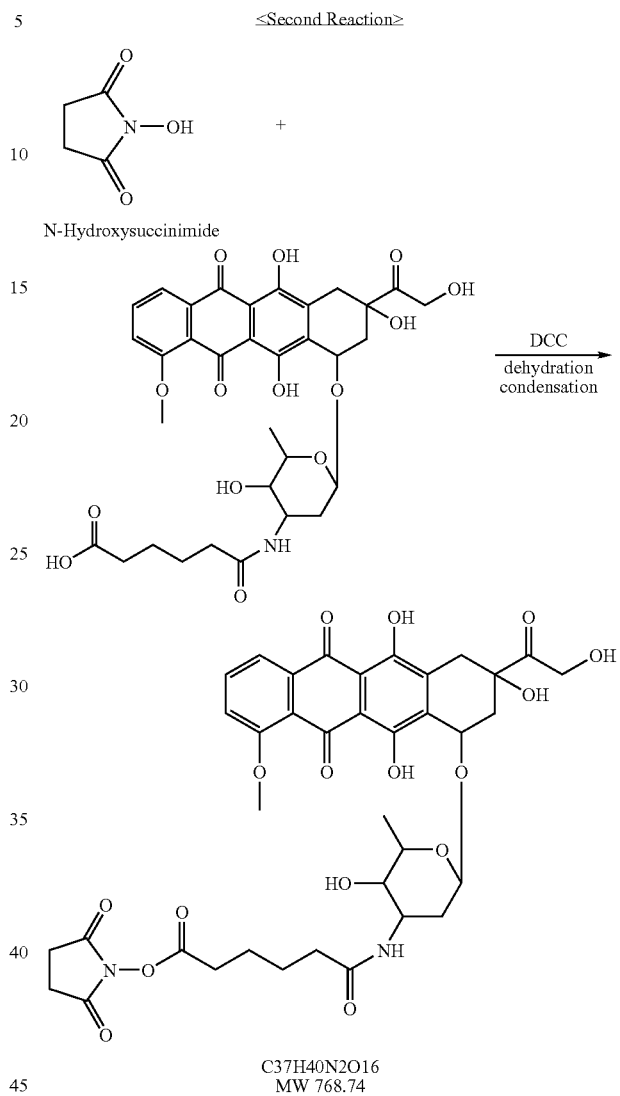

First, 3.81 mg of doxorubicin (Calbiochem Inc.), 1.79 mg of adipic anhydride, and 1.47 µL of triethylamine (TEA) were placed to a glass test tube equipped with a screw cap, and then tetrahydrofuran (THF) was added thereto up to a total volume of 3 mL. The mixture was allowed to react at 45° C. in a water bath for 48 hours.

After the reaction, a 1 µL, of the first reaction mixture was removed and diluted with 49 µL of methanol, and the first reaction product was confirmed by TLC and LC/MS. With TLC, the first reaction product spot was detected above the doxorubicin spot. With LC/MS, the doxorubicin was detected at a retention time (RT) of 3.00 min, and the first reaction product was detected at RT 5.39 min. The results are shown in FIG. 3.

Figure 3:
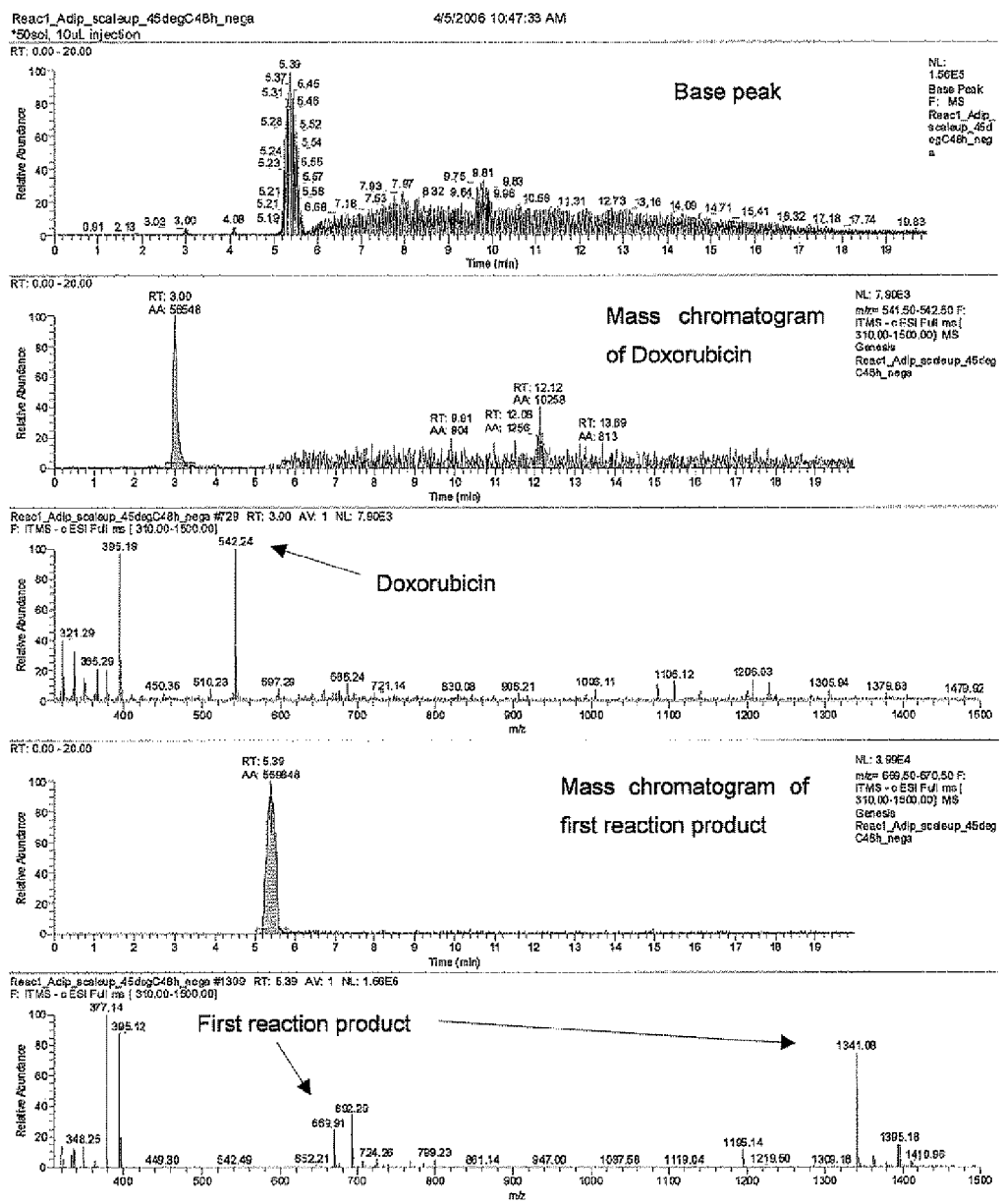
FIG. 3 shows an LC chromatogram, and mass chromatograms and mass spectra for both doxorubicin and the first reaction product, for confirming the first reaction product.

In the mass spectrum of FIG. 3, the first reaction product is the ion detected at m/z 669.91, and it is thought that m/z 1341.08 is a dimmer of the first reaction product due to ionization.

Next, the eluate at retention times from 4.50 to 6.00 min was collected and dried by spraying $N_2$ gas at 40° C., and the precipitate was dissolved in 3 mL of THF. It was confirmed by LC/MS that the first reaction product had been concentrated.

To the resultant THF solution of the first reaction product, 1.52 mg of N-hydroxysuccinimide and 1.68 mg of N,N'-dicyclohexylcarbodiimide (DCC) was added, and the mixture was allowed to react at 45° C. in a water bath for 30 hours.

After the reaction, a 1 µL of the second reaction solution was removed and diluted with 49 µL of methanol, and the second reaction product was confirmed by TLC and LC/MS. With TLC, the second reaction product spot was detected below the first reaction product spot and above the doxorubicin spot. With LC/MS, the first reaction product was detected at RT 8.10 min, and the second reaction product was detected at RT 7.81 min. The results are shown in FIG. 4.

Figure 4:
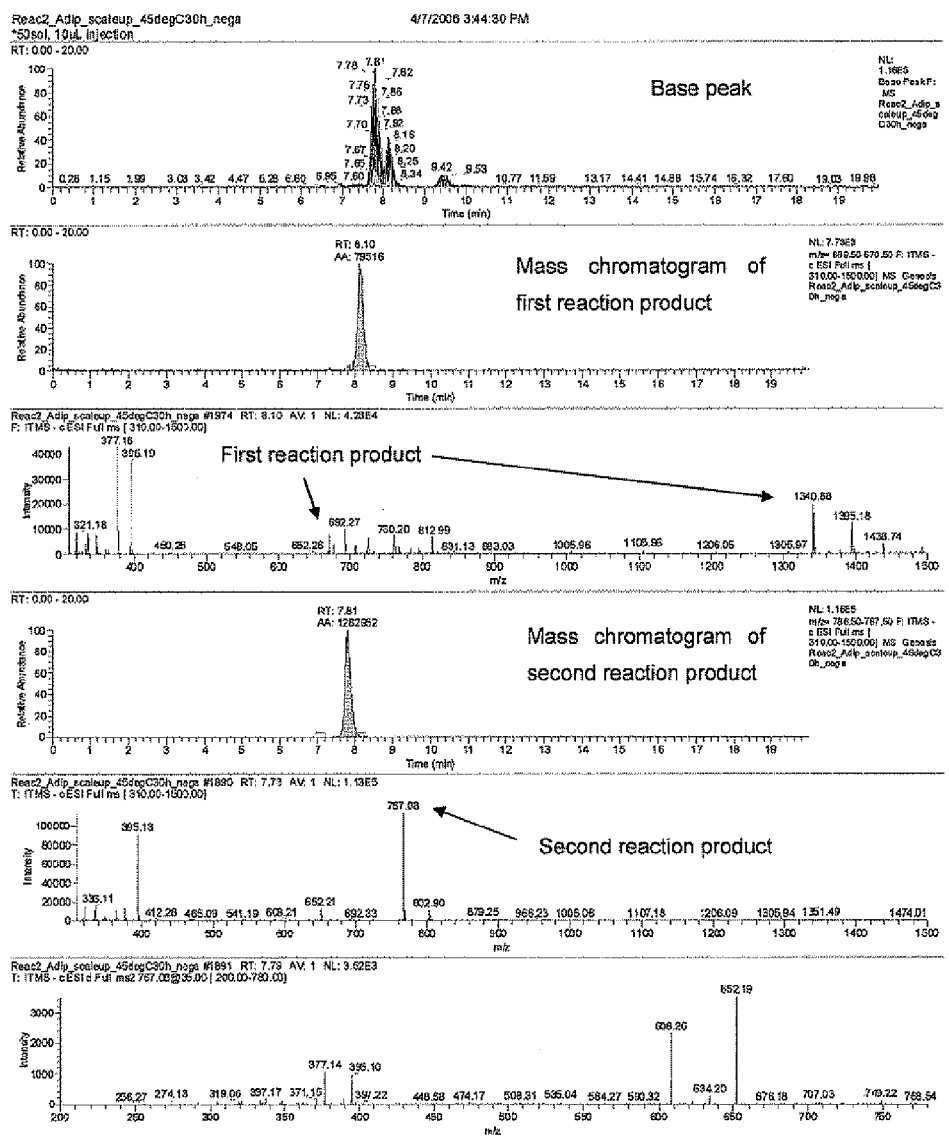
FIG. 4 shows an LC chromatogram, and mass chromatograms and mass spectra for both the first reaction product and the second reaction product, for confirming the second reaction product.
Figure 5:
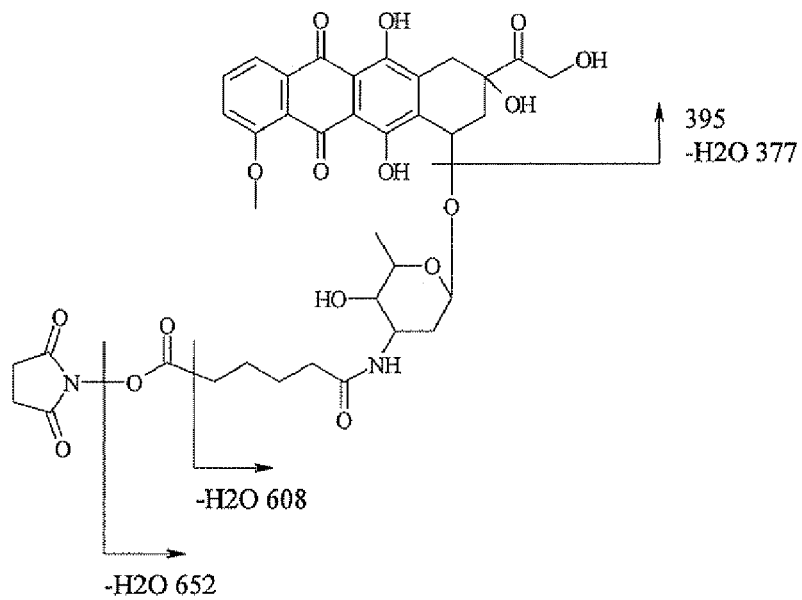
FIG. 5 is a diagram for illustrating the fragmentation of the second reaction product.

In the mass spectrum of FIG. 4, the second reaction product is the ion detected at m/z 767.08. The $MS^2$ spectrum when m/z 767.08 serves as the precursor ion also strongly shows that this is the target compound of the second reaction (see the fragmentation of the second reaction product shown in FIG. 5).

Next, the insoluble solid was removed with a 0.22 µm filter, and then the reaction mixture was dried by spraying $N_2$ gas at 40° C., and the precipitate was dissolved in 3 mL of 0.2 M NaHCO$_3$/0.5 M NaCl solution (pH 8.3). The residue that was not redissolved was removed with a 0.22 μm filter, thereby purifying the second reaction product.

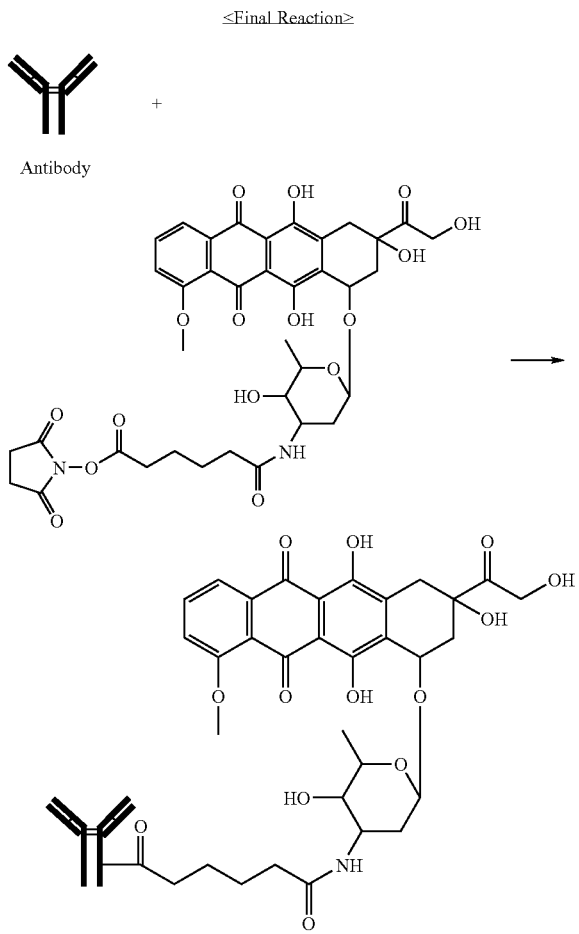

To the solution containing the second reaction product described above, 20 μL of Anti (MAP) Type XIV Collagen serum (LSL Co.) was added immediately and the mixture was allowed to react at room temperature for one hour. The second reaction product and the reacted protein group were separated by gel filtration chromatography. Thereby, 137 fractions (5 mL each) were obtained. The final reaction product is thought that antibody is conjugated with the anticancer drug doxorubicin via a spacer.

Of these fractions, fraction numbers 117 and 125 exhibited relatively dark color (red) that is believed to be derived from the doxorubicin. Based on the assumption of an antibody concentration of 8.0 mg/mL in serum, the concentration of the final reaction product in both of these fractions was calculated to be approximately $2 \times 10^{-7}$ M.

Example 4

Investigation of Antitumor Activity of Doxorubicin-Conjugated Anti-Collagen XIV Antibody Against Cultured Breast Cancer Cells The antitumor activity against the cultured breast cancer cells of fraction numbers 117 and 125 obtained in Example 3 was evaluated with 3-(4,5-dimethylthiazol-2-yl)-5-(3-carboxymethoxyphenyl)-2-(4-sulphophenyl)-2H-tetrazolium method (MTS; U.S. Pat. No. 5,185,450), which is a modification of the 3-(4,5-dimethyl-2-thiazolyl)-2,5-diphenyl-2H tetrazolium bromide (MTT) assay.

The Hs. 578T cell strain (collagen XIVα1 is expressed: ATCC HTB-126™), a breast cancer established cultured cell line, was plated in a 96-well plate at a density of $2 \times 10^3$ cells/90 μL, and precultured for 24 hours. Cultivation was performed at 37° C. in a 5% v/v CO$_2$ atmosphere using Dulbecco Modified Eagle's Medium (D-MEM (high glucose): Invitrogen Corp.-Gibco) supplemented with 0.01 mg/mL bovine insulin (SIGMA) and 10% v/v fetal bovine serum (Hyclone). The culture medium was changed with a fresh medium, and the fraction numbers 117 and 125 were added thereto at an antibody concentration of $2 \times 10^{-8}$ M or $1 \times 10^{-9}$ M and then cultured. It should be noted that Hank's balanced solution was used to dilute the antibody. A medium to which antibody was not added was similarly cultured as a control. After 24 and 48 hours, MTS (CeliTiter 96® AQueous One Solution Cell Proliferation Assay, Promega Corporation Madison, Wis., USA) was added according to the manual, and after two hours the absorbance at 490 nm was measured with a plate reader. The resulting values were statistically evaluated with a t-test. The results are shown in FIG. 6.

Figure 6:
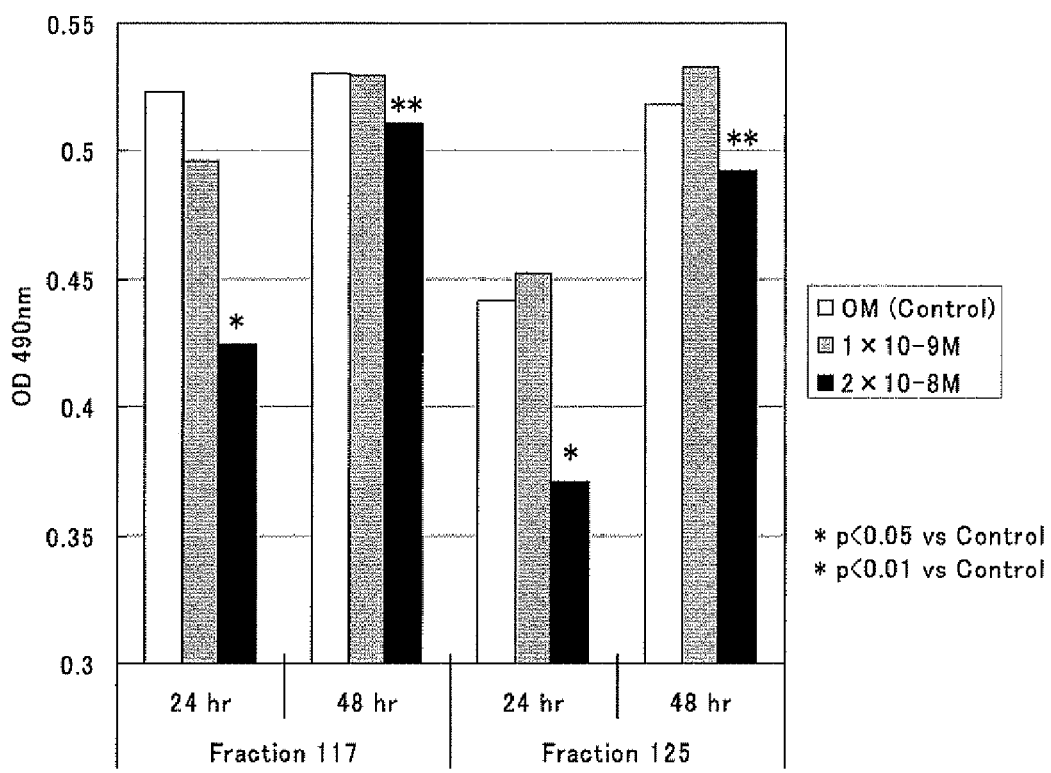
FIG. 6 is a graph that shows the absorbance at 490 nm of the cultured breast cancer cells, after addition of fraction numbers 117 and 125, which contain the final reaction product.

As seen from FIG. 6, in both fraction numbers 117 and 125, a significant drop in absorbance at an antibody concentration of $2 \times 10^{-8}$ M was observed, and it tends to be concentration dependent. Consequently, it was confirmed that doxorubicin-conjugated anti-collagen XIV antibody has the effect of preventing breast cancer cell growth.

According to the present invention, it is possible to easily and accurately detect and diagnose high malignancy breast cancer. Thus, it is possible to judge the degree of malignancy of the breast cancer and to establish a preoperative and postoperative auxiliary chemotherapy regimen against the breast cancer. The estimation of a prognosis based on the degree of malignancy and the determination of cancer individuality is essential for the tailor-made medicine in recent years. Against high malignancy breast cancer, the selection of systemic therapy by combination of chemotherapy and radiotherapy is required. Thus it is important for increasing survival time and improving their QOL to diagnose the grade of malignancy based on prognosis factors and biomarkers, to select preoperative and postoperative chemotherapy and to develop rapid treatment based on this diagnosis. If the therapeutic agent for breast cancer of the present invention is used, then high malignancy breast cancer can be treated efficiently.

The invention claimed is:

1. A method for detecting high malignancy breast cancer in a breast tissue or a breast cancer (primary or metastatic) tissue, comprising:
   bringing the tissue into contact with an antibody against collagen XIV or antigen-binding fragment thereof; and
   detecting the antibody or the antigen-binding fragment thereof bound to the tissue,
   wherein the detection of collagen XIV indicates a high malignancy breast cancer, and
   wherein the tissue has a higher level of collagen XIV as compared to a normal breast tissue.

* * * * *

UNITED STATES PATENT AND TRADEMARK OFFICE
CERTIFICATE OF CORRECTION

PATENT NO. : 8,030,014 B2
APPLICATION NO. : 11/993103
DATED : October 4, 2011
INVENTOR(S) : Yasushi Nakamura It is certified that error appears in the above-identified patent and that said Letters Patent is hereby corrected as shown below:

Title Page, Column 2, Other Publications, Line 36, delete "Ennis" and insert -- Ehnis --

Signed and Sealed this
Tenth Day of January, 2012

David J. Kappos
*Director of the United States Patent and Trademark Office*